United States Patent
Zhou et al.

(10) Patent No.: US 10,526,217 B2
(45) Date of Patent: Jan. 7, 2020

(54) METHOD FOR PRODUCING ACRYLIC ESTER WITH LOW POLLUTANT DISCHARGE

(71) Applicant: Chinese Research Academy of Environmental Sciences, Beijing (CN)

(72) Inventors: Yuexi Zhou, Beijing (CN); Yudong Song, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 0 days.

(21) Appl. No.: 16/095,785

(22) PCT Filed: Apr. 21, 2017

(86) PCT No.: PCT/CN2017/081430
§ 371 (c)(1),
(2) Date: Oct. 23, 2018

(87) PCT Pub. No.: WO2017/190599
PCT Pub. Date: Nov. 9, 2017

(65) Prior Publication Data
US 2019/0127244 A1    May 2, 2019

(30) Foreign Application Priority Data

May 6, 2016 (CN) .......................... 2016 1 0299240

(51) Int. Cl.
*C02F 1/469* (2006.01)
*C07C 67/08* (2006.01)
(Continued)

(52) U.S. Cl.
CPC .............. *C02F 1/4693* (2013.01); *B01D 3/36* (2013.01); *B01J 31/0225* (2013.01);
(Continued)

(58) Field of Classification Search
CPC ...... B01D 61/42; B01D 61/422; B01D 61/44; B01D 61/445; B01D 61/46; B01D 61/50;
(Continued)

(56) References Cited

U.S. PATENT DOCUMENTS 4,274,969 A * 6/1981 Lecoq ...................... C02F 1/66
                                                    210/721
4,536,269 A * 8/1985 Chlanda ............... B01D 61/445
                                                    204/535
(Continued)

FOREIGN PATENT DOCUMENTS

CN    101591245 A    12/2009
CN    102020552 A    4/2011
(Continued)

OTHER PUBLICATIONS

Chinese Second Office Action—Application No. 201610299240.5—dated Jul. 30, 2018.
(Continued)

*Primary Examiner* — David C Mellon
(74) *Attorney, Agent, or Firm* — Amster, Rothstein & Ebenstein LLP

(57) ABSTRACT

The present application discloses a method for producing acrylate with low pollutant discharge. The method has the advantages of high raw material utilization efficiency, low concentration, low salinity and low toxicity of wastewater pollutant, easy treatment of wastewater and etc.

8 Claims, 5 Drawing Sheets

(51) Int. Cl.
*C07C 67/54* (2006.01)
*C07C 69/54* (2006.01)
*C07C 67/48* (2006.01)
*B01D 3/36* (2006.01)
*B01J 31/02* (2006.01)
*C02F 103/36* (2006.01)
*C02F 101/34* (2006.01)

(52) U.S. Cl.
CPC .............. *C07C 67/08* (2013.01); *C07C 67/48* (2013.01); *C07C 67/54* (2013.01); *C07C 69/54* (2013.01); *B01D 2257/70* (2013.01); *C02F 2101/34* (2013.01); *C02F 2103/36* (2013.01)

(58) Field of Classification Search
CPC .... B01D 61/52; B01D 61/54; B01D 2311/02; B01D 2311/04; B01D 2311/06; B01D 2311/08; B01D 2311/10; B01D 2311/106; B01D 2311/12; B01D 2311/25; B01D 2311/26; B01D 2311/2649; B01D 2311/2669; B01D 2311/2696; B01D 3/36; B01D 2257/70; C02F 1/469; C02F 1/4693; C02F 2103/36; C02F 2101/34; B01J 31/0225; C07C 69/54; C07C 67/54; C07C 67/52; C07C 67/48; C07C 67/08
See application file for complete search history.

(56) References Cited

U.S. PATENT DOCUMENTS 5,522,995 A * 6/1996 Cockrem ............. B01D 61/025
210/259

5,645,703 A * 7/1997 Tsai ..................... B01D 61/445
204/538

FOREIGN PATENT DOCUMENTS

| | | |
|---|---|---|
| CN | 102206562 A | 10/2011 |
| CN | 102225976 A | 10/2011 |
| CN | 102276017 A | 12/2011 |
| CN | 103406091 A | 11/2013 |
| CN | 103408175 A | 11/2013 |
| CN | 103408176 A | 11/2013 |
| CN | 103435737 A | 12/2013 |
| CN | 103588935 A | 2/2014 |
| CN | 104254549 A | 12/2014 |
| CN | 105293642 A | 2/2016 |
| CN | 105968002 A | 9/2016 |
| DE | 102008060218 A1 * | 6/2010 ............. C07C 67/08 |
| JP | H029793 A | 1/1990 |
| WO | 03048103 A | 6/2003 |
| WO | 2010063529 A1 | 6/2010 |
| WO | 2013160702 A1 | 10/2013 |

OTHER PUBLICATIONS

Chinese Notice of Allowance—Application No. 201610299240.5—dated Jan. 8, 2019.
Chinese Office Action dated Nov. 16, 2017 issued in connection with Chinese Application No. 201610299240.5.
Tanaka Y, entitled "Development of a computer simulation program of feed-and-bleed ion-exchange membrane electrodialysis for saline water desalination," Desalination 342 (2014), 126-138.
German Office Action dated Sep. 24, 2019 issued in connection with German Application No. 11 2017 002 337.8.

* cited by examiner

METHOD FOR PRODUCING ACRYLIC ESTER WITH LOW POLLUTANT DISCHARGE

TECHNICAL FIELD

The present application relates to a method for producing acrylates, and particularly, to a method for producing acrylates with low pollutant discharge.

BACKGROUND

Acrylate is an extremely important basic raw material and intermediate in modern chemical industry, which is widely used in many applications such as adhesives, coatings, plastics, textiles, paper making, leather, elastomers, printing, synthetic fibers, building materials, superabsorbent resins, anti-scaling of boilers, UV/EB curing, flocculant, additive industry and detergent industry.

The wastewater discharged from the acrylate production device usually has the characteristics of high salt content, high organic matter concentration, high toxicity and difficulty in treatment, wherein the total dissolved solids (TDS) is up to 50-120 g/L, and the chemical oxygen demand (COD) is up to 30,000-90,000 mg/L. The main pollutants in the wastewater are sodium acrylate and catalysts of sodium salts which, depending on the catalyst, may be sodium p-toluenesulfonate, sodium methanesulfonate or sodium sulfate. Due to the high salt content, difficulty in treatment and that it is not suitable for incineration treatment, the treatment is mainly carried out by a biological treatment after significant dilution. However, the biological treatment system is low in load, large in area, and susceptible to impact, and the effluent water quality is unstable.

On the one hand, the acrylate wastewater has high concentration of pollutants, is difficult to handle and has high treatment cost; on the other hand, the wastewater contains high concentration of sodium acrylate, which has resource values. Therefore, how to convert the organic acid salts with high concentration in the wastewater into useful resources is the key for the treatment of acrylate wastewater.

At present, a number of patents have been proposed to utilize the acrylic acid in the wastewater from the acrylate devices to realize the resource utilization, such as production of modified lignosulfonate (CN103588935A), boiler scale inhibitor (CN103408175A), adsorption resin (CN103435737A), titanate adsorbent (CN103406091A), soaping agent (CN102206562A), dispersing agent (CN102225976A), and the like. Although the concentration of pollutants in acrylate wastewater is high, when it is used as a raw material to produce products, the total amount is relatively small, resulting in a small scale of production. Furthermore, it is required to establish a separate production device, which has high operation and maintenance costs, often has no economic value, and thus is difficult to apply in pollution control practices. Therefore, it is necessary to develop a process for utilizing the wastewater resource within the acrylate production process to reduce the concentration of pollutants discharged from the production process.

SUMMARY OF THE INVENTION

The technical problem to be solved by the present application is to provide a method for producing an acrylate with low pollutant discharge. A conventional acrylate production process is shown in FIG. 1. The method of the present application is an improvement to the conventional acrylate production process, which reduces pollutant discharge in the wastewater, recycles the available resources in the wastewater and achieves an unexpectedly high conversion of acrylic acid.

In one aspect, the present application provides a method for producing an acrylate with low pollutant discharge, characterized in that the method comprises the following steps:

(1) subjecting an acrylic acid, a catalyst and an alcohol to an esterification reaction in an esterification reactor to produce an esterified product;

(2) washing the esterified product of step (1) with water to recover the catalyst and the unreacted acrylic acid, and recycling the recovered catalyst and the unreacted acrylic acid back to the esterification reactor;

(3) washing the esterified product with an alkali after water washing to further remove the organic acid in the product;

(4) rectifying the esterified product after the alkali washing, and removing the light components and the heavy components to obtain products;

wherein the method further comprises:

(5) collecting a wastewater phase containing the wastewater produced by alkali washing, and recovering alcohols and esters in the wastewater phase, wherein the recovery is preferably carried out by a distillation tower;

(6) treating the wastewater produced after recovering the alcohol and the ester in step (5) by a multi-stage bipolar membrane electrodialysis system to recover the organic acid solution and the alkali solution therein;

(7) subjecting the recovered organic acid solution to an acidification treatment, followed by a dehydration treatment, and then recycling back to the esterification reactor of step (1). Preferably, the recovered alkali solution is recycled back to the production process, for example, for neutralization of acidic wastewater from acrylic acid production in the upstream of the acrylate production process, or for the alkali washing of step (3).

In one embodiment, the esterification reactor has a salt crystal collection structure.

In one embodiment, the catalyst of the present application is an organic sulfonic acid or sulfuric acid solution, the alcohol is butanol or octanol. Preferably, the organic sulfonic acid is methanesulfonic acid and p-toluenesulfonic acid.

In one embodiment, the esterification reactor of the present application comprises four or five compartments in series, wherein the last compartment is provided with a salt crystal collection structure. The salt crystal collection structure is a cylinder protruding outward from the bottom of the compartment, the bottom of the cylinder is provided with a discharge valve. The bottom of the compartment has a slope inclined to the crystal collection structure, and the slope is >5%. Preferably, the catalyst and the unreacted acrylic acid recovered in step (2) are recycled back to the first compartment of the esterification reactor.

In one embodiment, the alkali washing of the esterified product of the present application is carried out with a 15 wt % to 20 wt % sodium hydroxide solution, and/or an alkali solution having corresponding concentration (for example, 15 wt % to 20 wt %) formulated by the alkali solution recovered in step (6).

In one embodiment, the organic acid solution recovered in step (6) is acidified, and then dehydrated by azeotropic distillation with the alcohol used in the esterification of step (1) as an azeotropic agent. Preferably, the acidification treatment is carried out in step (7) with a regenerated anion exchange column. Preferably, the activated carbon adsorption column can be used for the treatment prior to the acidification treatment with a regenerated anion exchange column. Particularly, after the acidification treatment with an anion exchange resin column, the recovered organic acid solution of the present application is dehydrated by azeotropic distillation with the alcohol (for example, butanol or octanol) used in the esterification of step (1) as an azeotropic agent. Preferably, the azeotropic agent contains 0.1 wt % to 0.2 wt % of a polymerization inhibitor having a boiling point of 90° C. or higher, which is sprayed from the upper portion of the dehydration tower in an amount of 5% to 20%, based on the mass of the recovered organic acid solution. The treated organic acid solution enters from the middle of the tower, and the temperature of the dehydration tower is controlled at 80 to 85° C. After condensing of the overhead steam, the layers are separated in the tank. The organic phase is refluxed back to the dehydration tower and the reflux flow is 2 to 5 times of the amount of the organic acid solution; the aqueous phase enters the overhead tank of the dehydration tower of the esterification reactor. After the dehydration treatment, the water content of the organic acid solution is reduced to 20 wt % to 30 wt %. The organic acid solution is mixed with acrylic acid and catalyst and then enters the esterification reactor, for example, the first compartment of the esterification reactor. The activated carbon adsorption column of the present application employs activated carbon particles with a particle size of 1 to 5 mm, and the contact time is 0.5 to 2 h. After the adsorption is saturated, the activated carbon adsorption column is firstly regenerated by low-temperature alkali washing with NaOH aqueous solution, and then regenerated by steam at a high temperature. The anion exchange resin column is provided with an anion exchange resin. The resin particles have a particle size of 1 to 2 mm and the contact time of 2 to 12 minutes. When the treatment efficiency is lowered, the resin is firstly regenerated by alkali washing with NaOH aqueous solution, and then replaced with an acrylic acid solution before reuse. The wastewater discharged by regeneration with the NaOH aqueous solution is mixed with water phase discharged from the alcohol recovery tower, and then subjected to recovery treatments with the organic acid and alkali.

The resource utilization of alkali solution recovered in the present application can be achieved by two routes: route 1 is used in the neutralization of the wastewater from acrylic acid production in the acrylate production device; and route 2 is used in the alkali washing section of the acrylate unit in the acrylate production device.

In an embodiment of the present application, depending on the route of the resource utilization of alkali solution, the multi-stage bipolar membrane electrodialysis system of the present application employs different electrodialysis membrane stack structures: when the resource utilization of recovered alkali solution is achieved by route 1, the bipolar membrane electrodialysis membrane stacks employ a structure in which an anion exchange membrane and a bipolar membrane are alternately arranged; when the resource utilization of recovered alkali solution is achieved by route 2, the bipolar membrane electrodialysis membrane stacks employ a structure in which a bipolar membrane-an anion exchange membrane-a cation exchange membrane are alternately arranged.

Preferably, the multi-stage bipolar membrane electrodialysis system of the present application is a bipolar membrane electrodialysis device having 2 to 5 stages, i.e. a system in which 2 to 5 bipolar membrane electrodialysis devices of the same type are connected in series.

Before treatment with the bipolar membrane electrodialysis according to the present application, the wastewater is subjected to pretreatments such as cooling, filtration, ion exchange, etc. to lower the temperature and remove suspended matters, colloids and multivalent cations.

Preferably, in the anion exchange membrane used in the multi-stage bipolar membrane electrodialysis system of the present application, the mass transfer coefficient of acrylic acid therein is 0.001 dm/h or less, wherein the acrylic acid has one or more group selected from the group consisting of —$NH_2$, —NHR and —$NR_2$, wherein R is an organic functional group; preferably, R is methyl, ethyl or propyl.

The mass transfer coefficient of acrylic acid in the anion exchange membrane is the amount of 1 mol/L of acrylic acid mass transferred into the desalted water by penetration per unit area of the anion exchange membrane per unit time without an applied electric field.

Preferably, the multi-stage bipolar membrane electrodialysis system of the present application is multiple bipolar membrane electrodialysis devices using the same kind of membrane stack structure. When the bipolar membrane electrodialysis membrane stacks employ a structure in which the bipolar membrane—the anion exchange membrane—the cation exchange membrane are alternately arranged, the initial solution in the feed chamber of each stage device is acrylate wastewater after pretreatment such as cooling, filtration, ion exchange, and the like; the initial solution in the acid chamber of the first stage device is desalted water or a solution containing a corresponding catalyst; the initial solution in the alkali chamber is desalted water or sodium hydroxide solution; the initial solution in the acid chamber of the subsequent device is the organic acid solution recovered in the device of the prior stage; and the initial solution in the alkali chamber is the alkali solution recovered in the device of the prior stage. When the bipolar membrane electrodialysis membrane stacks employ a structure in which an anion exchange membrane and a bipolar membrane are alternately arranged, the initial solution in the feed chamber of each stage device is the acrylate wastewater after pretreatment such as cooling, filtration, ion exchange, and the like; the initial solution in the acid chamber of the first stage device is desalted water or a solution containing a corresponding catalyst; the initial solution in the acid chamber of the subsequent device is the organic acid solution recovered in the device of the prior stage. By this process, the number of bipolar membrane electrodialysis devices required by multi-stage bipolar membrane electrodialysis system is greatly reduced. In an embodiment of the present application, the acrylate production device of the present application has a final drainage chemical oxygen demand (COD) of 1000 to 3000 mg/L and the acrylic acid concentration of 200 to 2000 mg/L.

In a particularly preferred aspect of the present application, the present application discloses a particularly preferred method for producing acrylates with low pollutant discharge, characterized in that, the method comprises steps of:

(1) subjecting an acrylic acid, a catalyst (such as sulfuric acid or organic sulfonic acid, such as methanesulfonic acid and p-toluenesulfonic acid) and an alcohol (such as butanol or octanol) to an esterification reaction in an esterification reactor to produce an esterified product, the esterification reactor has a salt crystal collection structure;

(2) washing the esterified product of step (1) with water to recover the catalyst and the unreacted acrylic acid, and recycling the recovered catalyst and the unreacted acrylic acid back to the esterification reactor;

(3) washing the esterified product with an alkali after water washing to further remove the organic acid in the product;

(4) rectifying the esterified product after alkali washing, and removing the light components and the heavy components to obtain a product;

wherein the method further comprises:

(5) combining the wastewater from the above esterification reaction, the wastewater produced during the recovery of the catalyst and the unreacted acrylic acid and the wastewater from the alkaline washing to produce a wastewater phase, recovering the alcohol and the ester in the wastewater phase, and then subjecting the wastewater to the pretreatments such as cooling, filtration and ion exchange, and the like;

(6) treating the wastewater after the pretreatment in step (5) by a multi-stage bipolar membrane electrodialysis system to recover the organic acid solution and the alkali solution therein; wherein the multi-stage bipolar membrane electrodialysis system is 2 to 5 bipolar membrane electrodialysis devices using the same type of membrane stack structure; when the bipolar membrane electrodialysis membrane stacks employ a structure in which a bipolar membrane-an anion exchange membrane-a cation exchange membrane are alternately arranged, the initial solution in the feed chamber of each stage device is the acrylate wastewater after the pretreatment in step (5); the initial solution in the acid chamber of the first stage device is desalted water or a solution containing a corresponding catalyst, and the initial solution in the alkali chamber is desalted water or a sodium hydroxide solution; the initial solution in the acid chamber of the subsequent device is the organic acid solution recovered in the device of the prior stage; and the initial solution in the alkali chamber is the alkali solution recovered in the device of the prior stage; when the bipolar membrane electrodialysis membrane stacks employs a structure in which an anion exchange membrane and a bipolar membrane are alternately arranged, the initial solution in the feed chamber of each stage device is the acrylate wastewater after pretreatment in step (5); the initial solution in the acid chamber of the first stage device is desalted water or a solution containing a corresponding catalyst; the initial solution in the acid chamber of the subsequent device is the organic acid solution recovered in the device of the prior stage;

(7) subjecting the recovered organic acid solution to an acidification treatment, followed by a dehydration treatment, and then recycling back to the esterification reactor of step (1) for esterification reaction.

Using the above method, the COD in the drainage of the acrylate production device is reduced by more than 90% compared with the conventional process, and the salinity is reduced to 3000 mg/L or less.

The acrylate production method of the present application has the following advantages.

(1) Resource recycling of the organic acid salts in the acrylate wastewater is realized, and the pollutant discharge, the salinity, toxicity and handling difficulty of the wastewater are reduced.

(2) Resource utilization of the recovered organic acid solution and sodium hydroxide solution within the device are realized. A newly established utilizing device for recovering materials is not required. The method has small investment, low operating cost, does not depend on other production devices, and is convenient for the modification of existing devices.

(3) The method does not introduce new impurities during the recovery of organic acids, and the water content is reduced to 20 wt % to 30 wt %. The recycled organic acids are used in the acrylate production process without adversely affecting production efficiency and product quality.

(4) In the traditional process for recovering the organic acids from the organic acid salt wastewater by a bipolar membrane electrodialysis, it needs to perform a concentration by a two-chamber type electrodialysis first, and then a treatment by a bipolar membrane electrodialysis. Each ion of organic acid salt need to pass through the ion exchange membrane twice successively during the electrodialysis for concentrating and the bipolar membrane electrodialysis, resulting in a relative high energy consumption for recovering organic acids. The method of the present application directly treats the acrylate wastewater by a multi-stage bipolar membrane electrodialysis system, and simultaneously completes the concentration of ions and the conversion of organic acids, wherein the organic acid ions only need to pass through the ion exchange membrane once. Compared with the traditional process, the present method can reduce 35% or more of electrodialysis energy consumption.

(5) By providing a salt crystallization device on the basis of the conventional esterification reactor, the adverse effects such as corrosion on equipment and an increase of polymer brought by the small amount of sodium salt contained in the recovered organic acids during the production are effectively prevented.

A method for producing acrylates with low pollutant discharge of the present application will be further described below with reference to the accompanying drawings.

DETAILED DESCRIPTION

The applicant hereby illustrates the following examples for exemplary purposes only. It should be understand that these examples are not to be construed as limiting the present application in any way.

In the embodiment of the present application wherein a multi-stage bipolar membrane electrodialysis system is used, when the bipolar membrane electrodialysis membrane stacks employ a structure in which a bipolar membrane-an anion exchange membrane-a cation exchange membrane are alternately arranged, the initial solution in the feed chamber of each stage device is the acrylate wastewater after the pretreatment in step (5); the initial solution in the acid chamber of the first stage device is desalted water or a solution containing a corresponding catalyst, and the initial solution in the alkali chamber is desalted water or sodium hydroxide solution; the initial solution in the acid chamber of the subsequent device is the organic acid solution recovered in the device of the prior stage, and the initial solution in the alkali chamber is the alkali solution recovered in the device of the prior stage. When the bipolar membrane electrodialysis membrane stacks employ a structure in which an anion exchange membrane and a bipolar membrane are alternately arranged, the initial solution in the feed chamber of each stage device is the acrylate wastewater after pretreatment in step (5); the initial solution in the acid chamber of the first stage device is desalted water or a solution containing a corresponding catalyst; the initial solution in the acid chamber of the subsequent device is organic acid solution recovered in the device of the prior stage.

COMPARATIVE EXAMPLE

Figure 1:
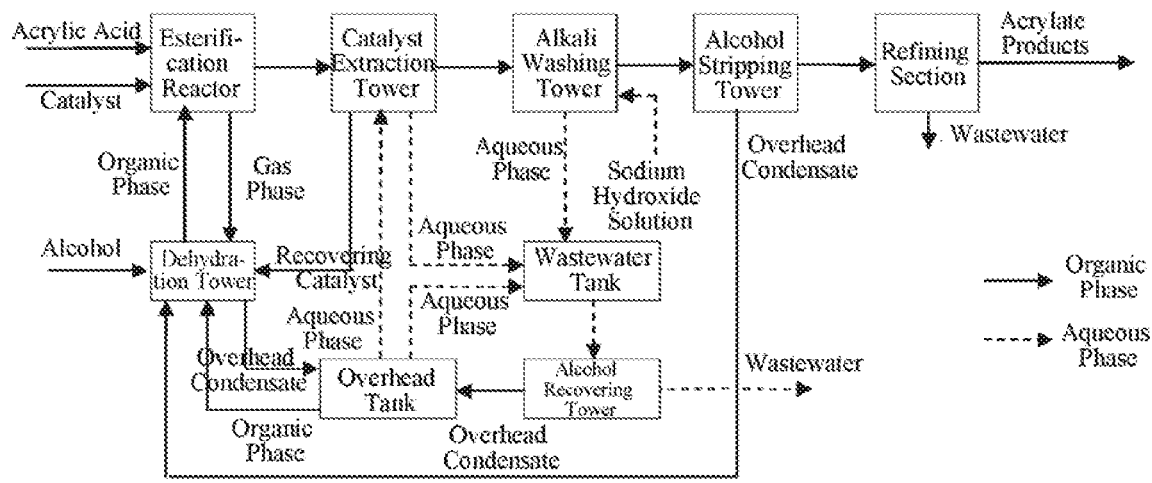
FIG. 1 shows a conventional process route for producing acrylates.

The butyl acrylate was produced by the conventional production route shown in FIG. 1. For the wastewater discharged from the alcohol recovery tower, the COD concentration was 46,500 mg/L, the acrylate anion concentration was 30,000 mg/L, and the p-toluenesulfonate anion concentration was 6,700 mg/L.

Example 1

Figure 2:
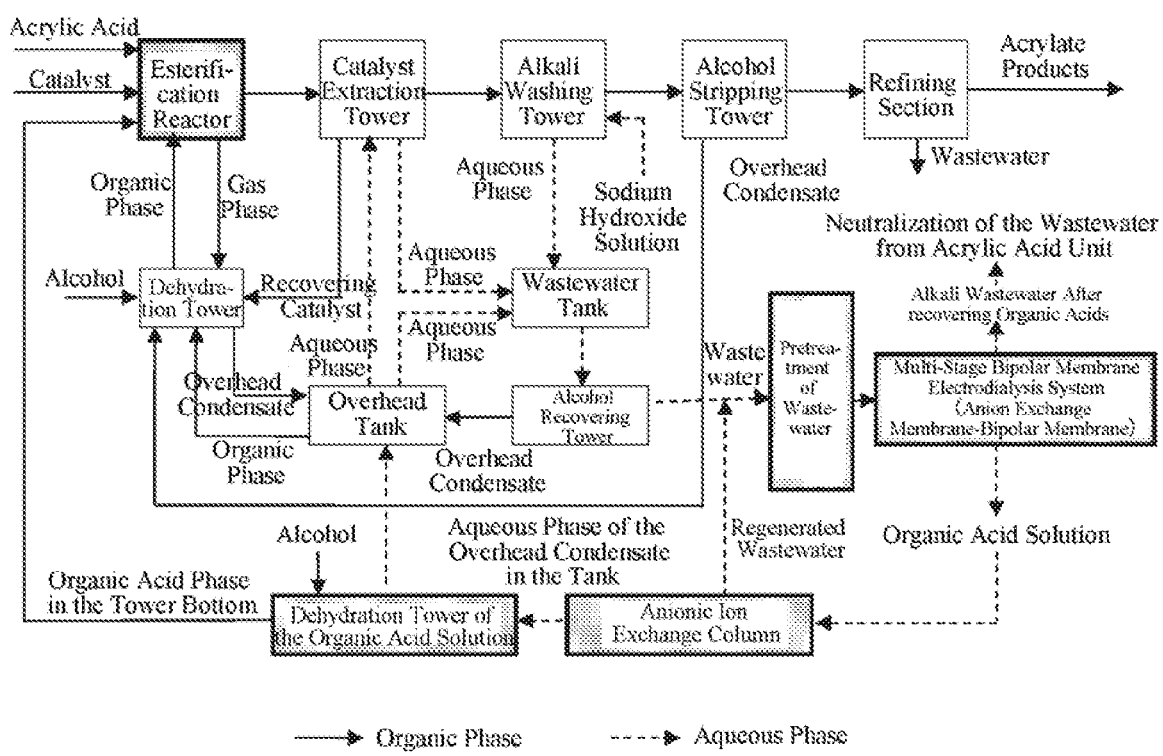
FIGS. 2 and 3 are process routes for producing acrylates according to the method of the present application, which show that the recovered sodium hydroxide solution is used for neutralization of the acidic wastewater from the acrylic acid production unit of the acrylate production device (route 1), and for the alkali washing section of the acrylate unit of the acrylate production device (route 2), respectively.
Figure 3:
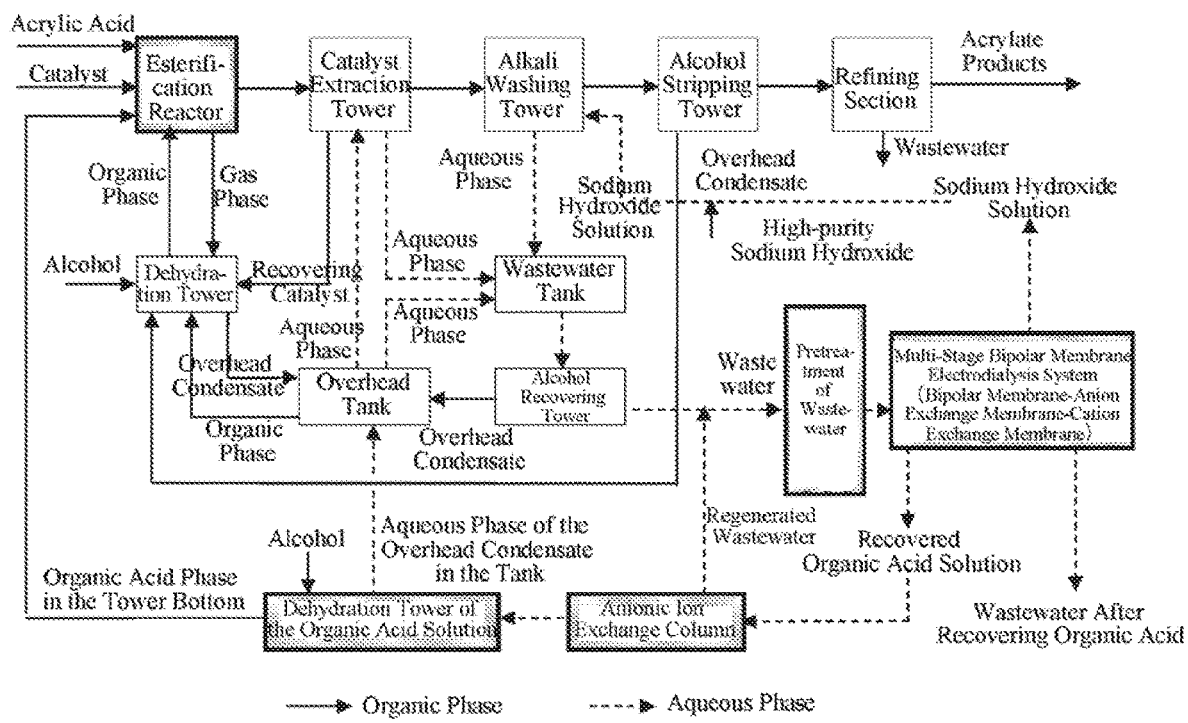
Figure 4:
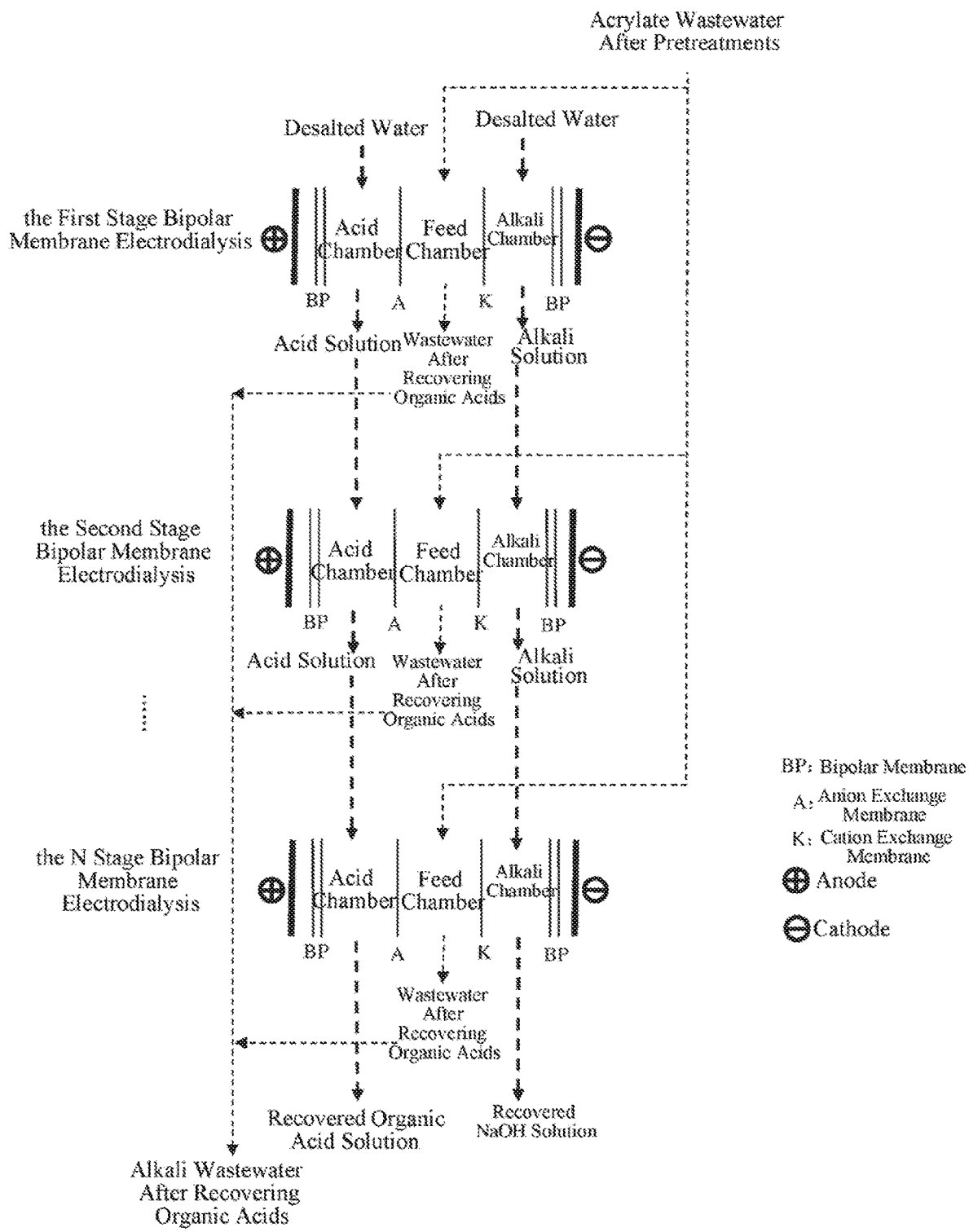
FIG. 4 is a schematic diagram of a multi-stage bipolar membrane electrodialysis system (wherein a bipolar membrane-an anion exchange membrane-a cation exchange membrane are alternately arranged).

The production process was modified according to the process route of FIG. 2. The wastewater discharged from the alcohol recovery tower was subjected to pretreatments such as cooling, filtering, ion exchange and the like, followed by a treatment of a 3-stage bipolar membrane electrodialysis system (wherein a bipolar membrane-an anion exchange membrane-a cation exchange membrane were alternately arranged; FIG. 4, N=3). In the discharged wastewater, the COD concentration was 2,000 mg/L, the acrylate anion concentration was 980 mg/L and the p-toluenesulfonate anion concentration was 150 mg/L. The organic acid solution was recovered and subjected to the treatment by an anion exchange resin column, followed by a dehydration treatment, and then returned back to the production process. Some sodium hydroxide tablets were added to the recovered sodium hydroxide solution, until the concentration is up to 20% by weight, and then the resulted sodium hydroxide solution was used for alkali washing of the esterified product.

Example 2

The butyl acrylate was produced by the production route shown in FIG. 2. For the wastewater discharged from the alcohol recovery tower, the COD concentration was 43,000 mg/L, the acrylate anion concentration was 28,000 mg/L, and the p-toluenesulfonate anion concentration was 6,200 mg/L. The wastewater was subjected to pretreatments such as cooling, filtering, ion exchange and the like, followed by a treatment of a 4-stage bipolar membrane electrodialysis system (wherein a bipolar membrane-an anion exchange membrane-a cation exchange membrane were alternately arranged; FIG. 4, N=4, and the anion exchange membrane had a —NH$_2$ group). In the discharged wastewater, the COD concentration was 2,230 mg/L, the acrylate anion concentration was 970 mg/L and the p-toluenesulfonate anion concentration was 126 mg/L. The recovered organic acid solution contained 194,000 mg/L of acrylic acid and 42,300 mg/L of p-toluenesulfonic acid. The electrodialysis energy consumption for recovering organic acid is 1.53 kWh/kg.

Example 3

Figure 5:
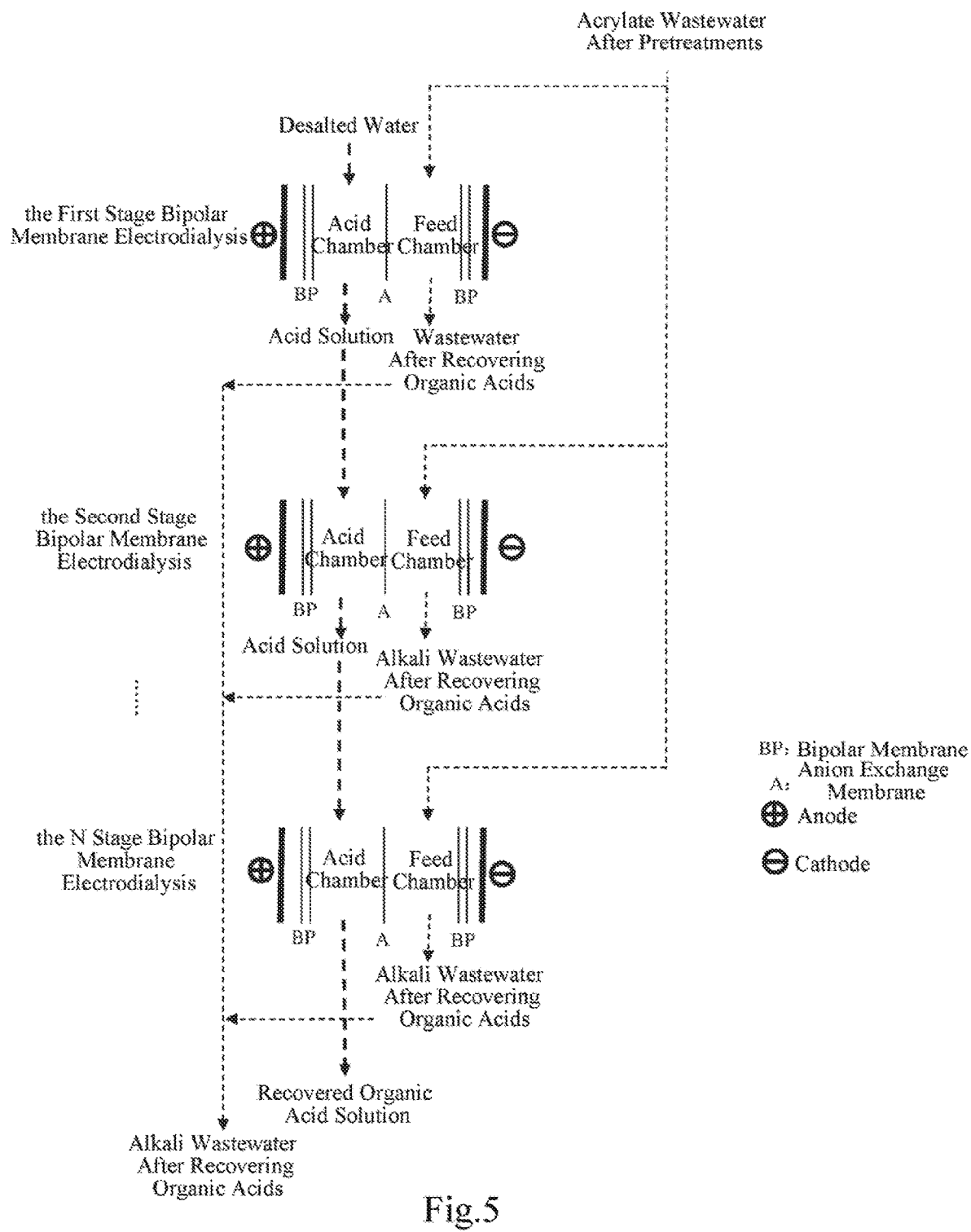
FIG. 5 is a schematic diagram of a multi-stage bipolar membrane electrodialysis system (wherein an anion exchange membrane and a bipolar membrane are alternately arranged).

For the wastewater discharged from the alcohol recovery tower of the butyl acrylate device, the acrylate anion concentration was 40,000 mg/L and the p-toluenesulfonate anion concentration was 8,000 mg/L. After pretreatments and a treatment of a 4-stage bipolar membrane electrodialysis system (wherein an anion exchange membrane and a bipolar membrane were alternately arranged; FIG. 5, N=4, the anion exchange membrane had a —NHR group and R is methyl), the recovered organic acid solution contained 200,000 mg/L of acrylic acid and 40,000 mg/L of p-toluenesulfonic acid. The alkali content in alkali wastewater after recovering organic acid is 2.3%. After recovering the organic acid, the alkali wastewater was used for neutralization of acidic wastewater in the acrylic acid production unit. The recovered organic acid solution was subjected to a treatment by an anion exchange resin column. The anion exchange resin column was filled with a macroporous weakly alkaline anion exchange resin, the resin particles had a particle size of 1 to 2 mm and a contact time was 12 minutes. Butanol containing 0.2% by weight of a polymerization inhibitor (hydroquinone) was used as a dehydrating agent for the treated organic acid, which was sprayed from the upper part of the dehydration tower in amount of 10%, based on the mass of the recovered organic acid solution. After acidification treatment by ion exchange, the organic acid solution entered from the middle of the tower, and the temperature of the dehydration tower was controlled at 85° C. The overhead vapor was condensed and then the layers were separated in the tank. The organic phase was refluxed back to the dehydration tower and the reflux flow was 5 times of the amount of organic acid solution; the water phase entered the overhead tank of the dehydration tower of the esterification reactor. After the dehydration treatment, the water content in the organic acid solution was reduced to 20%. The organic acid solution was mixed with acrylic acid and catalyst, and entered the first compartment of the esterification reactor. The esterification reactor contained five compartments in series, wherein the fifth compartment was provided with a salt crystal collection structure. After recovering the organic acid, the concentration of sodium acrylate in the wastewater was reduced to 1,780 mg/L, the concentration of sodium p-toluenesulfonate was reduced to 180 mg/L. Compared with the conventional process, the COD of the discharged wastewater was reduced by 94%.

Example 4

Figure 6:
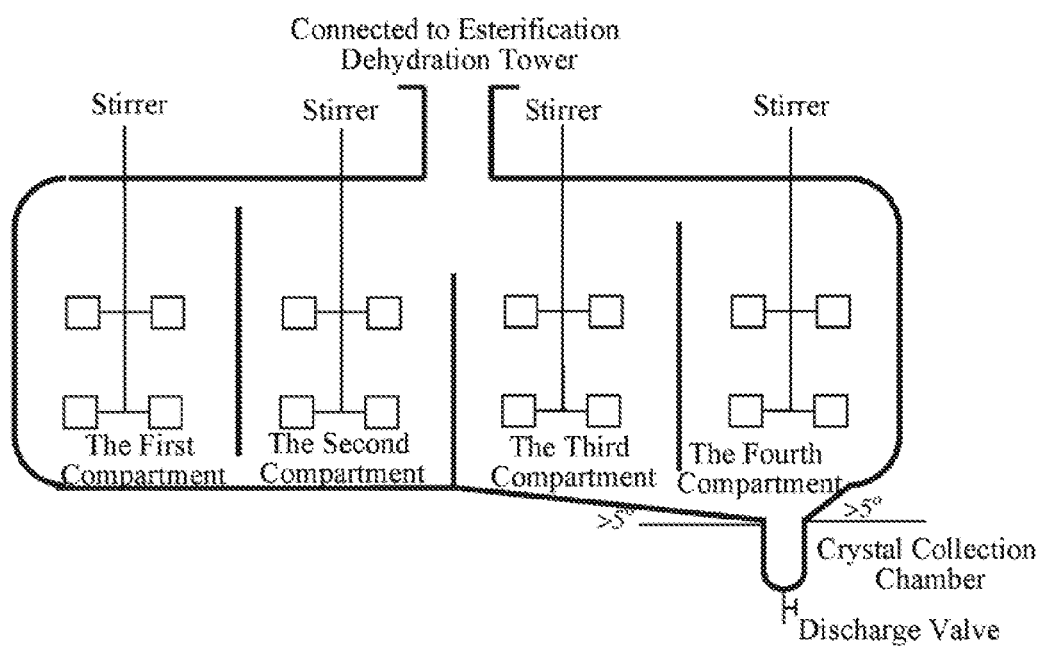
FIG. 6 is a schematic diagram of an esterification reactor with a salt crystal collection structure.

The isooctyl acrylate wastewater contained 30,000 mg/L of acrylate anion and 2,000 mg/L of sulfate anion. After the pretreatment and a treatment of a 3-stage bipolar membrane electrodialysis system (wherein an anion exchange membrane-a bipolar membrane-a cation exchange membrane were alternately arranged; FIG. 4, N=3, and the anion exchange membrane had a —NR$_2$ group and R was ethyl), the recovered organic acid solution contained 186,000 mg/L of acrylic acid and 11,000 mg/L of sulfuric acid. The alkali content in recovered alkali solution is 13%. After supplementing high-purity sodium hydroxide, the recovered alkali solution is used in the alkali washing section of the esterified product. The recovered organic acid solution was subjected to an acidification by an anion exchange resin. The anion exchange resin column was filled with a macroporous weakly alkaline anion exchange resin, the resin particles had a particle size of 1 to 2 mm and a contact time was 5 minutes. Butanol containing 0.1% by weight of a polymerization inhibitor (p-methoxyphenol) was used as a dehydrating agent for the treated organic acid, which was sprayed from the upper part of the dehydration tower in an amount of 20%, based on the mass of the recovered organic acid solution. After the ion exchange treatment, the organic acid solution entered from the middle part of the tower, and the temperature of the dehydration tower was controlled at 80° C. The overhead vapor was condensed and layers are separated in the tank. The organic phase was refluxed back to the dehydration tower and the reflux flow was 2 times of the amount of organic acid solution; the water phase entered the overhead tank of the dehydration tower of the esterification reactor. After the dehydration treatment, the water content in the organic acid solution was reduced to 30%. The organic acid solution was mixed with acrylic acid and catalyst, and entered the first compartment of the esterification reactor. The esterification reactor contained four compartments in series, wherein the fourth compartment was provided with a salt crystal collection structure (FIG. 6). For the drainage of the whole device, the concentration of acrylate anion was reduced to 1,500 mg/L, the concentration of sulfate ion was reduced to 90 mg/L. Compared with the conventional process, the COD of the discharged wastewater was reduced by 95% and the total dissolved solids were reduced to 2,500 mg/L.

Example 5

Acrylic acid, methanesulfonic acid and butanol were esterified in an esterification reactor to form butyl acrylate; the esterified product was washed with water to recover methanesulfonic acid and unreacted acrylic acid. The recovered methanesulfonic acid and unreacted acrylic acid were recycled back to the esterification reactor. The esterification reactor used was an esterification reactor with a salt crystal collection structure (FIG. 6). After washing with water, the esterified product was washed with alkali by using a 25 wt % NaOH solution to further remove the organic acid in the product; wherein the 25 wt % NaOH solution was obtained by recovering the 15 wt % NaOH solution from the multi-stage bipolar membrane electrodialysis and adding alkali tablets. After alkali washing, the esterified product was subjected to rectification to remove the light components and the heavy components and obtain a butyl acrylate product. The wastewater from alkali washing was mixed with the drainage of the overhead tank of the dehydration tower of the esterification reactor, and the drainage of the catalyst extraction tower, and then entered the alcohol recovery tower to recover butanol and butyl acrylate in the wastewater. The drainage of the alcohol recovery tower was subjected to pretreatments such as cooling, filtration and ion exchange and the like, and then to a treatment by 5-stage bipolar membrane electrodialysis device (FIG. 4, N=5; anion exchange membrane had —$NH_2$ and —NHR groups and R is a propyl), and the organic acid solution and the alkali solution therein were recovered. After an acidification treatment, the recovered organic acid solution was subjected to dehydration with butanol as a dehydrating agent, and then recycled back to the esterification reactor for esterification reaction. The recovered alkali solution was returned back to the alkali washing process of the esterified product. The conversion of acrylic acid in the entire production device reached 99.9%. For the drainage, the concentration of acrylate anion was reduced to 1,600 mg/L and the concentration of p-toluenesulfonate onion was reduced to 200 mg/L. If the esterification reactor employed a conventional reactor without a salt crystal collection structure, the conversion of the acrylic acid of the entire production device was 99.2% due to severe corrosion of the equipment, and the increased amount of the acrylic acid polymer.

Example 6

Acrylic acid, sulfuric acid and octanol were esterified in an esterification reactor to form octyl acrylate; the esterified product was washed with water to recover sulfuric acid and unreacted acrylic acid. The recovered sulfuric acid and unreacted acrylic acid were recycled back to the esterification reactor. The esterification reactor used was an esterification reactor with a salt crystal collection structure (FIG. 6). After washing with water, the esterified product was washed with alkali by using a 20 wt % NaOH solution to further remove the organic acid in the product. After alkali washing, the esterified product was subjected to rectification to remove the light components and the heavy components and obtain a butyl acrylate product. The wastewater of alkali washing was mixed with the drainage of the overhead tank of the dehydration tower of the esterification reactor and the drainage of the catalyst extraction tower, and then entered the alcohol recycle tower to recover octanol and octyl acrylate in the wastewater. The drainage of the alcohol recovery tower was subjected to pretreatments such as cooling, filtration, ion exchange and the like, then to a treatment by 3-stage bipolar membrane electrodialysis device (FIG. 5, N=3; anion exchange membrane had —$NH_2$, —NHR and —$NR_2$ groups and R is a methyl), and the organic acid solution and alkali solution therein were recovered. After an acidification treatment, the recovered organic acid solution was subjected to dehydration with octanol as a dehydrating agent, and then recycled back to the esterification reactor for esterification reaction. After recovering the organic acid, the alkali wastewater was used for neutralization of the wastewater from the acrylic acid production. The conversion of acrylic acid in the entire production device reached 99.9%. For the drainage, the concentration of acrylate anion was reduced to 1,400 mg/L and the concentration of sulfate anion was reduced to 70 mg/L.

The above examples are presented only for illustrating the preferred embodiments of the present application, which are not intended to limit the scope of the present application. Without departing from the spirit and scope of the present application, those skilled in the art can make any combinations on any technical features of the above embodiments. Meanwhile, without departing from the spirit and scope of the present application, those skilled in the art can make various modifications and improvements to the technical solutions of the present application, which should fall within the protection scope defined by the claims of the present application.

The invention claimed is:

1. A method for producing acrylates with low pollutant discharge comprising the following steps:
    (1) subjecting an acrylic acid, a catalyst and an alcohol to an esterification reaction in an esterification reactor to produce an esterified product;
    (2) washing the esterified product of step (1) with water to obtain a water-washed esterified product and recover the catalyst and any unreacted acrylic acid; and recycling the recovered catalyst and the unreacted acrylic acid back to the esterification reactor;
(3) washing the water-washed esterified product obtained from step (2) with an alkali;
(4) rectifying the esterified product obtained from step (3) to remove light components and heavy components, so as to obtain the acrylates;
wherein the method further comprises:
(5) collecting a wastewater phase containing wastewater produced by alkali washing in step (3), and recovering alcohols and esters in the wastewater phase to obtain a pretreated wastewater;
(6) treating the wastewater produced after recovering the alcohols and the esters in step (5) by a multi-stage bipolar membrane electrodialysis system to recover an organic acid solution and an alkali solution, wherein the multi-stage bipolar membrane electrodialysis system is made up of two to five bipolar membrane electrodialysis devices in series wherein each device has acid chamber confined by bipolar membrane and anion exchange membrane, feed chamber confined by anion exchange membrane and cation exchange membrane, and alkali chamber confined by cation exchange membrane and bipolar membrane, feed chamber is between acid chamber and alkali chamber,
the pretreated wastewater of step (5) is fed into feed chambers of the devices; desalted water is fed into the acid chamber of a first device and the effluent containing organic acid recovered flows into the acid chamber of next device; desalted water or sodium hydroxide solution is fed into the alkali chamber of the first device and the effluent containing alkali recovered flows into the alkali chamber of the next device;
(7) subjecting a recovered organic acid solution to an acidification treatment, followed by a dehydration treatment, and then recycling back to the esterification reactor of step (1) for esterification reaction.

2. The method according to claim 1, wherein the alkali solution recovered in step (6) is used for neutralization of acidic wastewater from a production of acrylic acid, or for the alkali washing of step (3).

3. A process according to claim 1, wherein the catalyst is an organic sulfonic acid or sulfuric acid solution and the alcohol is butanol or octanol.

4. The method according to of claim 1, wherein the esterification reactor comprises four or five compartments in series, wherein a last compartment of the four or five compartments in series is provided with a salt crystal collection structure, the salt crystal collection structure is a cylinder protruding outwardly from bottom of the last compartment, a discharge valve is provided at bottom of the cylinder, a slope inclined to the crystal collection structure is provided at bottom of the last compartment, and the slope is >5%.

5. The method according to of claim 1, wherein the alkali washing of the esterified product is carried out with a 15 wt % to 20 wt % sodium hydroxide solution, and/or a 15 wt % to 20 wt % alkali solution formulated with the alkali solution recovered in step (6).

6. The method according to claim 1, wherein the recovered organic acid solution is subjected to an additional acidification treatment, and then further dehydrated by azeotropic distillation with the alcohol used in the esterification of step (1) as an azeotropic agent.

7. The method according to claim 1, wherein prior to a treatment with the multi-stage bipolar membrane electrodialysis system, the wastewater is subjected to a pretreatment to lower the temperature and remove suspended matters, colloids and multivalent cations.

8. The method according to claim 1, wherein the esterification reactor has a salt crystal collection structure.

* * * * *